United States Patent [19]

Meistrell

[11] Patent Number: 4,700,406
[45] Date of Patent: Oct. 20, 1987

[54] ADJUSTABLY WRAPPABLE, STRETCHABLE STRAP FOR SHIN GUARD

[75] Inventor: William R. Meistrell, Manhattan Beach, Calif.

[73] Assignee: Dive N'Surf, Inc., Hermosa Beach, Calif.

[21] Appl. No.: 828,944

[22] Filed: Feb. 12, 1986

Related U.S. Application Data

[63] Continuation-in-part of Ser. No. 687,909, Dec. 31, 1984, Pat. No. 4,585,003.

[51] Int. Cl.$^4$ .......................... A41D 13/06; A41F 9/00
[52] U.S. Cl. .............................. 2/22; 2/338; 2/311; 2/232; 2/DIG. 6; 128/DIG. 15
[58] Field of Search ................. 2/22, 23, 24, DIG. 6, 2/232, 338, 311; 128/165, 327, DIG. 15; 36/2 R

[56] References Cited

U.S. PATENT DOCUMENTS

| | | | |
|---|---|---|---|
| 919,614 | 4/1909 | Meinecke . | |
| 1,345,906 | 7/1920 | Augustine . | |
| 3,086,529 | 4/1963 | Munz et al. | 2/311 X |
| 3,411,160 | 11/1968 | Le Roux et al. | 2/232 |
| 3,491,761 | 1/1970 | Baker . | |
| 3,880,161 | 4/1975 | Fossel | 128/DIG. 15 X |
| 3,889,684 | 6/1975 | Lebold . | |
| 4,040,124 | 8/1977 | Zoephel | 2/338 X |
| 4,044,773 | 8/1977 | Baldwin, III . | |
| 4,149,540 | 4/1979 | Hasslinger | 128/DIG. 15 X |
| 4,213,548 | 7/1980 | Wood | 2/DIG. 6 X |
| 4,273,130 | 6/1981 | Simpson | 2/338 X |
| 4,294,238 | 10/1981 | Woodford | 2/22 X |
| 4,497,070 | 2/1985 | Cho | 2/22 |
| 4,569,348 | 2/1986 | Hasslinger | 128/DIG. 15 X |

Primary Examiner—Louis K. Rimrodt
Assistant Examiner—J. L. Olds
Attorney, Agent, or Firm—William W. Haefliger

[57] ABSTRACT

A wrap means, for compressively wrapping an athlete's shin guard, comprising an insulative, flexible, relatively thin strap that is bi-directionally stretchable, the strap including a first elastomeric layer, and a second layer of pile fabric attached to and substantially covering the outer side of the first layer; the strap is adapted to be adjustably wrapped, and tensioned about a shin guard; and there are hook elements carried by the strap for removably attaching to the second layer at any position of wrap adjustment of the strap.

3 Claims, 7 Drawing Figures

ADJUSTABLY WRAPPABLE, STRETCHABLE STRAP FOR SHIN GUARD

BACKGROUND OF THE INVENTION

This application is a continuation-in-part of Ser. No. 687,909, filed Dec. 31, 1984, now U.S. Pat. No. 4,585,003.

This invention relates generally to stretchable wraps which are adjustable; and more particularly concerns an improved strap device which is adjustably wrappable through a wide range of wrap sizes, and easily attaches to a protective guard for limbs, as for example to a hockey player's shin guard, and at the same time allows adjustment of the guard, as during hockey play.

There is need for means to quickly and adjustably wrap about guards for limbs, such as shin guards, characterized by a wide range of wrap sizes; and this need is critical as respects athletes shin guards. Previously, wraps could not be quickly and easily changed as to tension exertion and position on shin guards, to accomodate to desired comfort and protection of the athlete wearer as well as expansion and contraction of the shin guard during leg movement.

SUMMARY OF THE INVENTION

It is a major object of the invention to provide apparatus meeting the above need, and which also provides additional advantages such as ease of attachment, ease of detachment; and flexibility and stretchability to best conform to the in-place shin guard which must accomodate to the athlete's leg movement. Basically, the device comprises:

(a) an insulative, flexible, relatively thin strap that is bi-directionally stretchable, the strap including a first elastomeric layer, and a second layer of stretchable pile fabric attached to and substantially covering the outer side of the first layer, (b) the strap adapted to be adjustably wrapped and to be adjustably tensioned, about the guard and with the pile fabric presented outwardly, and there being hook elements carried by the strap to removably attach to said second layer at any selected position of wrap adjustment of the endwise tensioned strap.

As will appear, the strap preferably has such stretchability as to be in at least partly stretched condition in use, conforming to the shifting position of the shin guard on the user's body (such as a limb), allowing the user to walk about with his limb resiliently compressively guarded and wrapped, and the strap easily affords different degrees of shin guard compression exertion on the body.

It is a further object of the invention to provide an improved device of the above character, wherein the thin elongated strap comprises an insulative, flexible, stretchable layer of material such as elastomer, foamed rubber being usable, and pile fabric covering one side of the elastomer layer, to allow a wide range of attachment points for hook tab means carried by the strap at one of its ends.

It is a further object of the invention to provide multiple such straps on and spaced along a shin guard, the straps each being individually adjustable to provide different degrees of tension to different zones on the shin guard, whereby the latter may be optimally fitted to a limb in compressive engagement therewith.

These and other objects and advantages of the invention, as well as the details of an illustrative embodiment, will be more fully understood from the following specification and drawings, in which:

DRAWING DESCRIPTION

DETAILED DESCRIPTION

Figure 3:
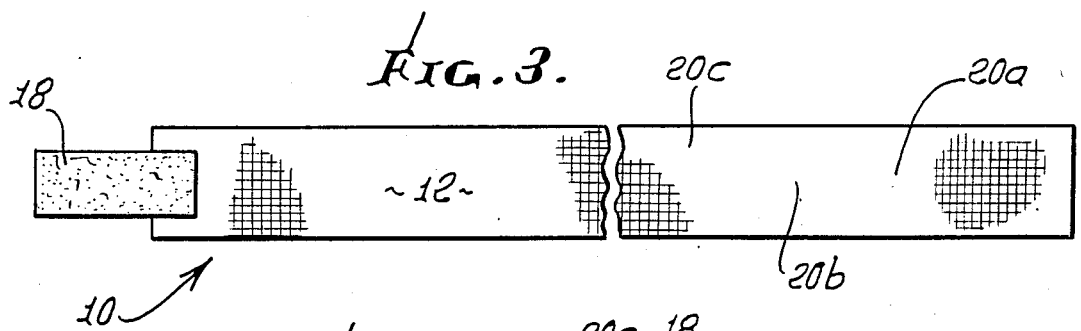
FIG. 3 is a plan view of a strap as used in FIG. 1.
Figure 4:
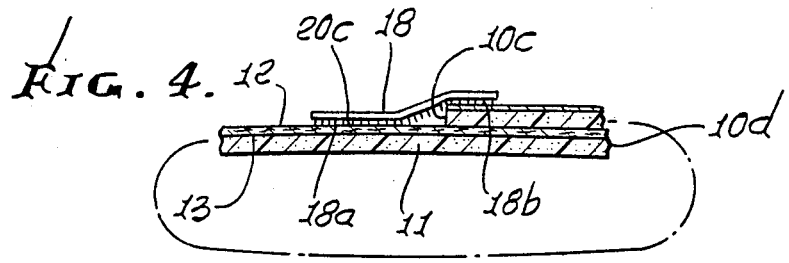
FIG. 4 is an enlarged fragmentary section showing the strap folded upon itself, a tab at one end attached to the outwardly presented pile fabric.

Referring first to FIGS. 3 and 4, a flexible, relatively thin strap 10 is bi-directionally stretchable, to accomodate widthwise reduction in dimension as the strap is stretched lengthwise. It includes a first elastomeric layer 11, and a second and thinner layer 12 of stretchable pile fabric attached to (as by bonding at 13) and substantially covering the outer side of the layer 11.

The strap has a width between 0.5 and 3 inches, and is optimally about 1.5 inches wide for hockey player shin guard wrapping. If less than 0.5 inch in width, its tension is insufficient for holding a shin guard 14 in sufficiently retained condition, and if wider than 3 inches, it is too close to a second strap 10 on the shin guard (see FIG. 1) so as to interfere with separate and independent wrapping and compressive retention (to different extents) of the straps on the guard. The strap length is between 10 and 24 inches, and optimally about 18 inches in length. If less than 10 inches, there is too little overlap of the strap sections, for good retention of the guard 14, and if greater than 24 inches, the strap becomes bulky and less easy to quickly wrap about the guard and attach to itself.

Figure 1:
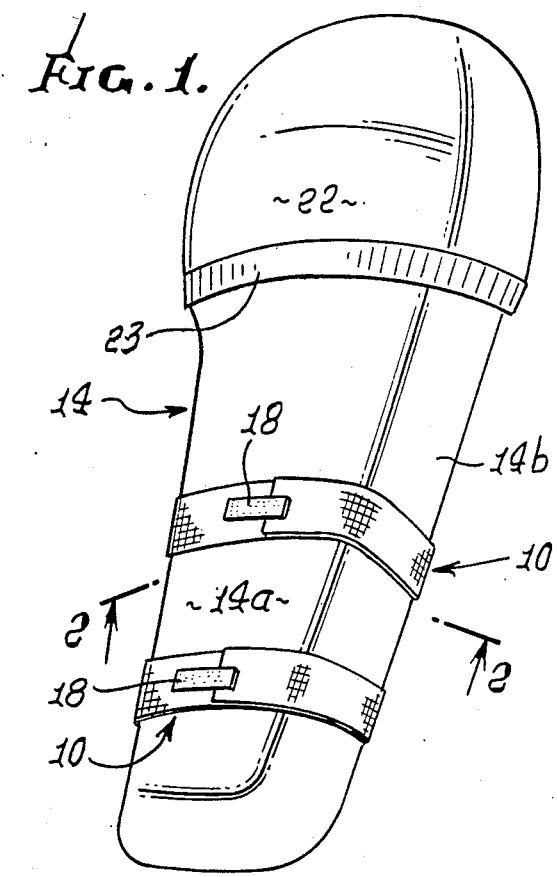
FIG. 1 is a perspective view of a hockey player's shin guard with wrap-type retention straps thereon.
Figure 2:
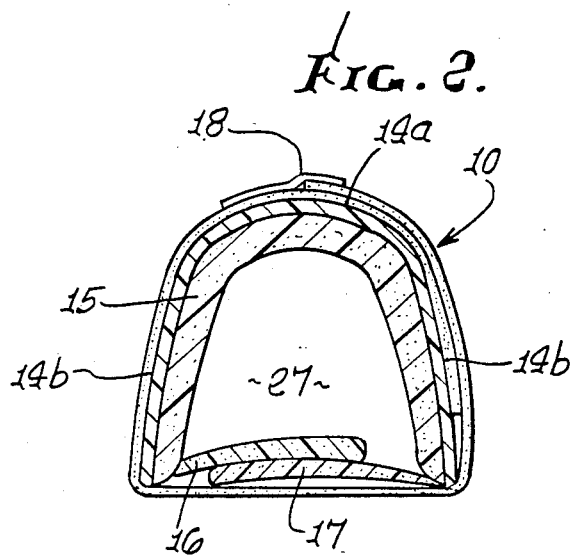
FIG. 2 is a section on lines 2—2 of FIG. 1.

The strap is adapted to be adjustably wrapped and tensioned about an athlete's protective limb guard, such as shin guard 14 of FIG. 1. That guard is U-shaped or channel shaped and may consist of a relatively stiff molded plastic section 14a which is longitudinally elongated, with U-shaped liner padding 15 in section 14a. Padding flaps 16 and 17 overlap at the open side of section 14a. A molded plastic knee cover 22 is attached at 23 to the upper end of the shin guard 14.

When the strap 10 is wrapped about the guard 14 and tensioned, it holds the side walls 14b of the guard compressively flexed inwardly toward the wearer's limb or shin, in zone 27. If the guard is too tight, the strap is quickly relieved and its tension reduced, to desired extent after which the strap is re-connected to hold the shin guard walls 14b in most comfortable position adjacent the limb.

The above is made possible by the use of multiple such straps, each independently adjustable, spaced apart along the guard 14, for example to allow a greater closure of the guard at its lower extent, and lesser closure of the guard at its upper extent, to grip different size portions of a limb, to about the same compressive extent.

These objectives are furthered by the provision of fabric tab means 18 attached to an end portion of the strap and carrying the hook elements, as at 18a. FIGS. 3 and 4 show that the tab means can be removably attached to any point of the pile fabric 12 covering layer 11, for example points 20a, 20b, 20c, etc. Opposite ends of the strap are shown at 10c and 10d. The attachment of the tab to end 10c, as at 18b, may be permanent.

The underlayer 11 consists of an elastomer such as foamed rubber (NEOPRENE) of a thickness between about 1/32 and ¼ inch. The strap 10 may be formed from the commercial product known as STARSKIN, 3 mm #1 smooth skin plush royal 403 produced by St. Albans Rubber Ltd., St. Albans, Herts, England.

Figure 5:
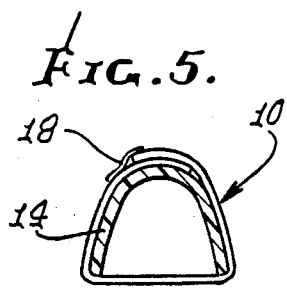
FIGS. 5, 6 and 7 are cross sections showing different extents of stretchable wrapping and compression exertions by a strap incorporating the invention.
Figure 6:
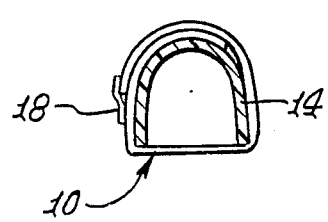
Figure 7:
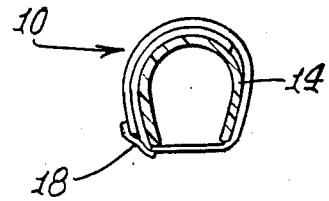

Such construction enables great versatility or adjustability of the strap, both as to exertion of a wide range of compressive forces, and use of the same strap on a wide range of shin guard expanded and contracted sizes. Thus, as shown in FIG. 5, the strap extends over guard 14, and extends about 390° about the guard; in FIG. 6, the same strap has been stretched about a lower section of the same guard to extend further about the latter, to exert greater compression on the shin guard to contract same about a smaller portion of the wearer's shin; and in FIG. 7, the same strap extends about a smaller shin guard, or guard section wrapped even more about the latter. This is made possible because the hooks on tab 18 may attach anywhere on the outer pile surface of the strap.

I claim:

1. Adjustable wrap means for wrapping about an athlete's shin guard whereby the tightness of the guard on the shin may be quickly adjusted, and in combination with said shin guard, said means comprising (a) two like, elongated, flexible, relatively thin straps each of which is bidirectionally stretchable, each strap including a first foam rubber layer, and a second layer of stretchable pile fabric attached to and substantially covering the entire outer side of the first layer, each strap having a length between 10 and 24 inches, and a width between ½ and 3 inches, the foam rubber thickness being between about 1/32 and ¼ inch, (b) each strap adjustably wrapped and adjustably tensioned, about said guard with said pile fabric presented outwardly, and tab means on each strap carrying hook elements, the tab means hook elements attached to an end portion of the strap second layer and projecting beyond said end portion to removably attach to said second layer at any selected position of wrap adjustment of the endwise tensioned strap, (c) said two straps spaced about and along the length of the shin guard, each shin guard being U-shaped in cross section along its length, there being U-shaped padding carried within a relatively stiff molded plastic outer section, one strap locally and adjustably compressively deflecting the guard and padding to greater extent than another strap.

2. The wrap means of claim 1 wherein said first layer comprises NEOPRENE foam.

3. The wrap means of claim 1 wherein the strap has the following dimensions:

(i) width, about 1½ inches,
    (ii) length, about 18 inches.

* * * * *